United States Patent [19]

Wolters et al.

[11] Patent Number: 4,489,674
[45] Date of Patent: Dec. 25, 1984

[54] METHOD FOR PRODUCTION OF A TRIPLOID CHANNEL CATFISH AND PRODUCT OF METHOD

[75] Inventors: William R. Wolters; Charles L. Chrisman; George S. Libey, all of West Lafayette, Ind.

[73] Assignee: Purdue Research Foundation, West Lafayette, Ind.

[21] Appl. No.: 238,101

[22] Filed: Feb. 25, 1981

[51] Int. Cl.³ .............................................. A01K 61/00
[52] U.S. Cl. ......................................................... 119/3
[58] Field of Search ............................................. 119/3

[56] References Cited
PUBLICATIONS

Terje Refstie, Vidar Vassvik and Trygve Gjedrem, "Induction of Polyploidy in Salmonids by Cytochalasin B", Aquaculture 10, 1977, pp. 65–74.

R. J. Valenti, "Induced Polyploidy in *Tilapia Aurea* (Steindachner) by means of Temperature Shock Treatment," J. Fish Biol. 1975, pp. 519–528.

Gary H. Thorgaard and Graham A. E. Gall, "Adult Triploids in a Rainbow Trout Family" Genetics 93, Dec. 1979, pp. 961–973.

*Primary Examiner*—Hugh R. Chamblee
*Attorney, Agent, or Firm*—Barnes & Thornburg

[57] ABSTRACT

A method for the induction of 100% triploidy in channel catfish by cold-shocking fertilized eggs at about 5° C. for up to about 1.0 hour starting about 5 minutes after fertilization.

3 Claims, 9 Drawing Figures

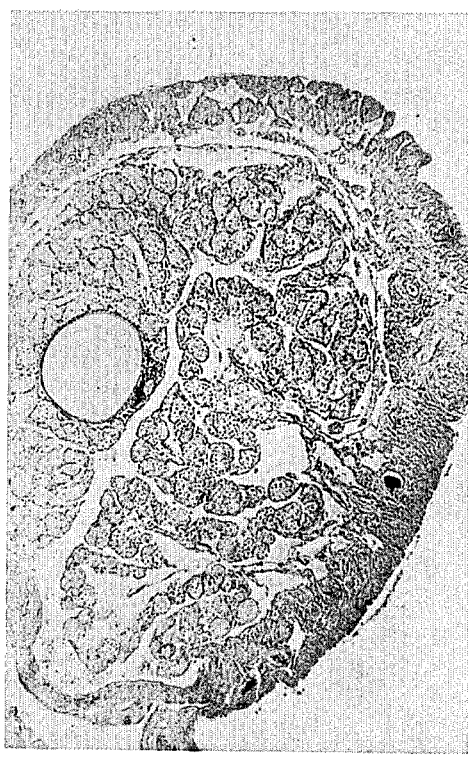
FIG. 3
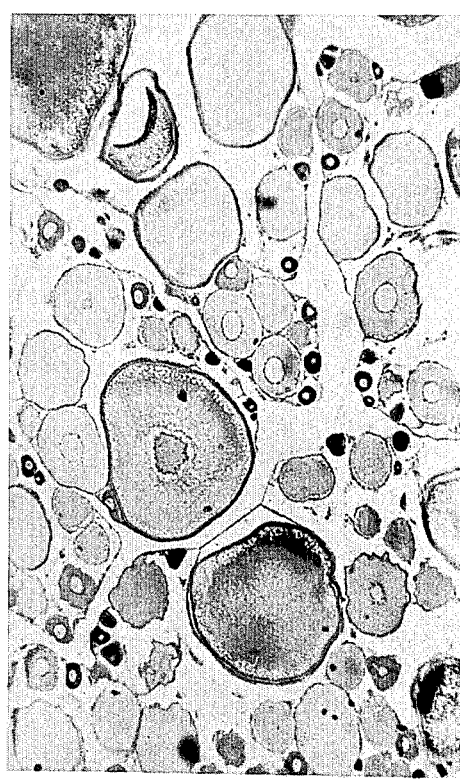
FIG. 4
FIG. 5
FIG. 6
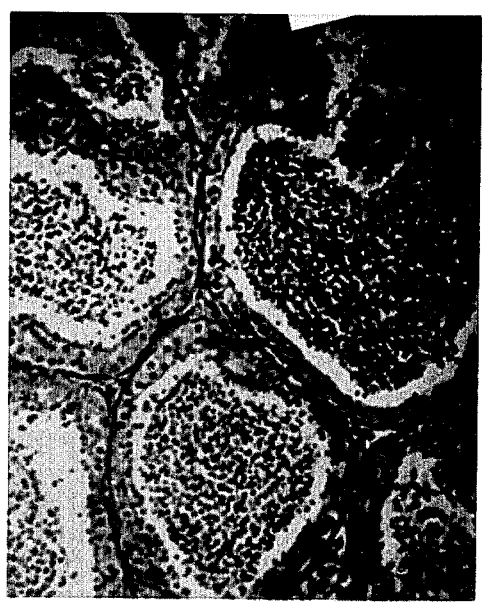

METHOD FOR PRODUCTION OF A TRIPLOID CHANNEL CATFISH AND PRODUCT OF METHOD

FIELD OF THE INVENTION

This invention is a method for the production of a sterile catfish with enhanced growth characteristics, and the catfish produced by the method is also claimed.

BACKGROUND OF THE INVENTION

Channel catfish (*Ictalurus punctatus*) are widely cultured because they are easily managed and have good food quality. Although much research has been performed on rearing, stocking, and nutrition of channel catfish, little research has been directed toward genetic improvements that would increase its value as a cultured species.

One genetic improvement that provides benefits to fish culture is the production of triploid (sterile) individuals. Triploidy is one type of polyploidy which may be generally described as a specimen with three complete sets of chromosomes in place of the usual two sets. Natural spontaneous triploidy in fish is rare. However, triploidy has been induced in certain fish species by cold-shocking fertilized eggs. For example, in the threespine stickleback *Gasterosteus aculeatus* as described by H. Swarup in "Production of triploidy in *Gasterosteus aculeatus* (L)," *Journal of Genetics*, 56:129-142, 1959a, cold-shocking was used for the purpose of inducing triploidy. However, using the suggested temperature and times the highest percentage of triploidy induced was 66.7%.

Again, respecting plaice and hybrid flounders a study was made and reported by C. E. Purdom in "Induced Polyploidy in plaice (*Pleuronectes platessa*) and its hybrid with the flounder (*Plathichthys flesus*)," Heredity, 49:11-24, 1975, using cold-shocking techniques to induce polyploidy. This study used different times and temperatures for application of the cold-shocking techniques and diploids, triploids, and even tetraploids were obtained. However, it was reported at page 16 of the article that "Survival percentages were similar in all groups up to 12 days after fertilisation, except for the triploid hybrids (italics supplied);this group of eggs showed catastrophic death rate for which no explanation could be found." However, after metamorphosis, it was reported that viability of triploids was as good for diploids produced by the cold-shock treatment. This study also claimed that of the fertilized eggs of the hybrid flounders treated that survived the cold-shock to hatching, all appeared to be triploids. No chromosome check was made but some data was presented which was claimed by Purdom to verify his conclusion.

Also, respecting the blue tilapia, cold-shocking was reported for the purpose of the induction of polyploidy by R. J. Valenti, "Induced polyploidy in *Tilapia aurea* (Steindachner) by means of temperature shock treatment," *J. Fish. Biol.*, 7:519-528, 1975. The results reported suggested that a cold shock at about 4° C. had a low percentage of hatch. After hatch, the mortality was described as low. It was recognized that using different temperature shocks as well as different durations of exposure, is highly significant. But no shock temperatures and exposure durations were disclosed which obtained consistent, or even verifiable by chromosome count (which was not done), obtention of triploidy fish. Even though it would appear that studies done with these and other species would suggest the present invention, the fact is that applicants are the first to devise a method for production of 100% triploid channel catfish.

THE DRAWINGS

FIG. 3 is a microphotograph of ovarian tissue of a female triploid channel catfish produced according to the present invention.

FIG. 4 is a microphotograph of ovarian tissue of a female diploid channel catfish used as a control.

FIG. 5 is a microphotograph of testicular tissue of a male triploid channel catfish produced according to the present invention.

FIG. 6 is a microphotograph of testicular tissue of a male diploid channel catfish used as a control.

DETAILED DESCRIPTION OF THE PREFERRED EMBODIMENT OF THE INVENTION

The Method

Figure 1:
FIG. 1 is a macrophotograph of diploid and triploid ovaries. Diploid specimen on bottom.

Two gravid female channel catfish were paired with male channel catfish in 1500 liter fiberglass tanks supplied with 5 liters per minute of aerated well water at 27° C. The fish were induced to ovulate with a daily injection (4.4 mg per kg) of carp pituitary extract. Spawning boxes were placed in the tanks for shelter. When the fish began ovulating, the eggs were hand-stripped and fertilized with sperm from mascerated testes of donor males.

Eggs from the first female to ovulate were divided into a control group and three treatment groups that were, respectively, cold-shocked at 5° C. for 1.0, 2.0, and 3.0 hours beginning 5 minutes after fertilization. Eggs from the second female were divided into a control group and two treatment groups were, respectively, cold-shocked at 5° C. for 1.0 and 1.5 hours beginning 5 minutes after fertilization. After treatment, the eggs were transferred without acclimation to a hatching tray having a freshwater inflow of 8 liters per minute of aerated well water at 27° C. The eggs were kept in screen-lined wire baskets and treated with malachite green for 30 seconds at 65 mg/liter at 12-hour intervals up to 24 hours before hatching to control fungus. The percentage of fertilization and hatching success was recorded for all treatment groups and controls.

Chromosome counts to determine ploidy were done on kidney tissue and culture lymphocytes. Kidney tissue was mascerated and treated for 30 minutes in vitro with colchicine. The cells were treated with 0.4% potassium chloride for 30 minutes and fixed in three changes of 3:1 methanol-acetic acid for 30 minutes. Blood for lymphocyte cultures was collected from the caudal vein and centrifuged. The separated leucocyte-rich plasma was placed in a culture bottle containing 10 ml Amphibian Culture Medium, 2 ml inactivated fetal bovine serum, 0.2 ml L-glutamine, 0.1 ml pokeweed mitogen, and 200 units penicillin, and 200 µg streptomycin per ml of culture medium. One hour prior to harvest, 40 µl of colcemid was added to arrest spindle development. Hypotonic action was accomplished with 0.4% potassium chloride for 30 minutes and fixation in three changes of 3:1 methanol-acetic acid. Cells were dropped into cold, wet slides, stained for 10 minutes in 4% Giemsa in pH 6.8 phosphate buffer. Metaphase plates were photographed through a Zeiss photomicroscope at 1000X on Kodak ® Panatomic X film developed in Microdol ®.

Chromosome counts were performed on 23 individuals from the control group and 22 from the cold-shocked group. Chromosome counts were made from at least 5 well-spread unbroken metaphase cells from each individual. The confidence interval for the percentage of ploidy in treatment groups was determined from the Clopper-Pearson procedure.

The Results

One female ovulated after two injections of carp pituitary extract. The percentage of fertilization determined from observation of viable embryos was high for all experimental groups according to the following Table 1:

TABLE 1

Responses of channel catfish eggs to cold shock.

|  | Hours of Cold Shock | No. of Eggs | Fertilization (%) | Hatching Success (%) | Incidence of Diploidy (%) | Incidence of Triploidy (%) |
|---|---|---|---|---|---|---|
| Female 1 | 0 (control) | 300 | 92 | 2 | 100 | 0 |
|  | 1.0 | 104 | 98 | 5 | 0 | 100 |
|  | 2.0 | 125 | 98 | 0 |  |  |
|  | 3.0 | 165 | 96 | 0 |  |  |
| Female 2 | 0 (control) | 100 | 98 | 89 | 100 | 0 |
|  | 1.0 | 107 | 100 | 79 | 0 | 100 |
|  | 1.5 | 106 | 99 | 0 |  |  |

Figure 8:
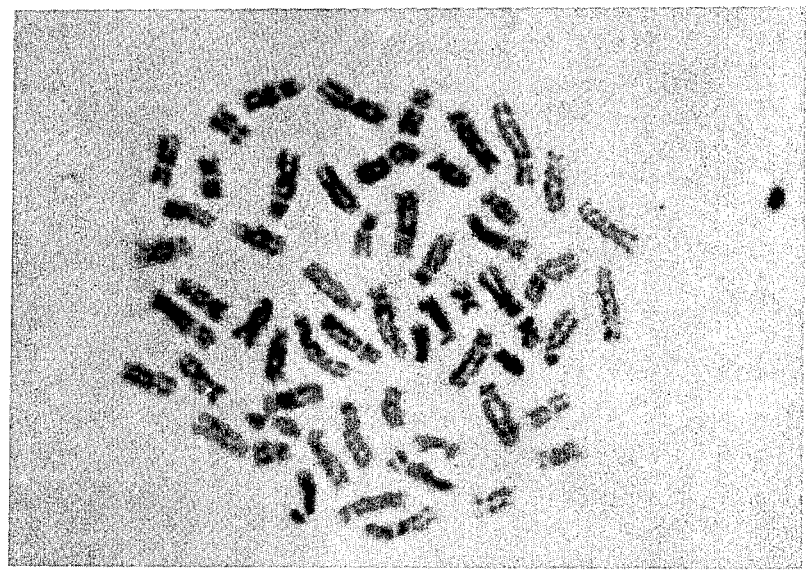
FIG. 8 is a microphotograph of a metaphase cell from a diploid channel catfish used as a control.
Figure 9:
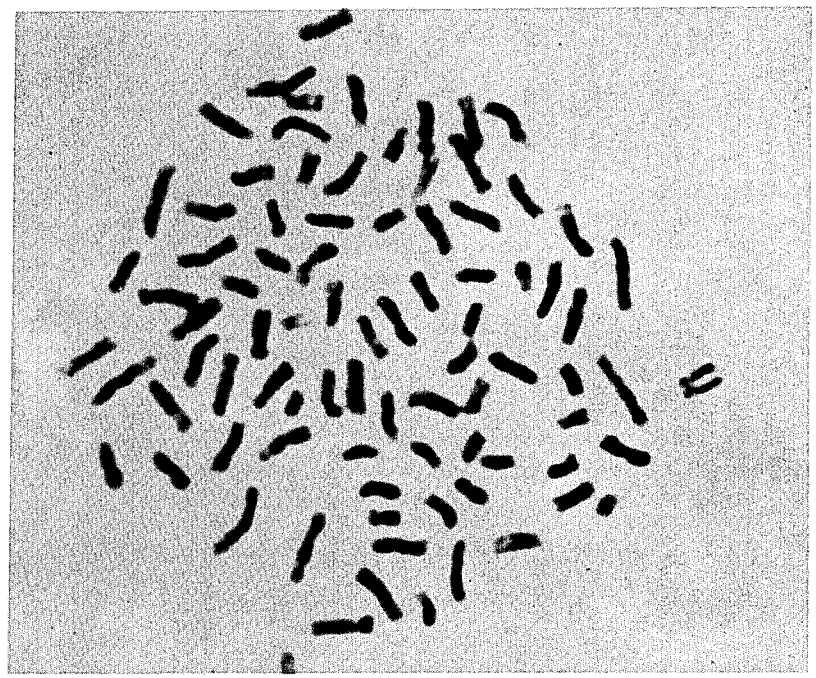
FIG. 9 is a microphotograph of a metaphase cell from a triploid channel catfish produced according to the present invention showing the chromosomes of the cell.

Eggs cold-shocked longer than 1-hour all died after 2-3 days incubation. The control group and the 1-hour cold-shocked group developed normally, but had a low hatching success because of a fungal invasion from pieces of mascerated testes remaining in the egg mass from the fertilization procedure. Surviving fry were reared until they approximated 5.0 cm in length, and then were sacrificed for karyotype analysis. All fish in the control group were diploid (2N=58; FIG. 8). In the 1-hour cold-shock group, the incidence of triploidy (3N=87; FIG. 9) was 100% (Table 1).

The second female ovulated after three injections. Because no eggs from the first female survived cold shocks 2.0 hours or longer, only 1.0- and 1.5-hour cold shocks were attempted. As before, the percentage of fertilization was high in all groups, and cold shocks longer than 1-hour caused total mortality after 2-3 days of incubation (Table 1). Eggs from the control and 1-hour treatment groups developed normally and had hatching successes of 89% and 79%, respectively. The surviving fry were again reared to approximately 5.0 cm before chromosome analysis was attempted. All fish analyzed from the control group were diploid (FIG. 8). All first analyzed from the 1-hour cold-shock group were triploid (FIG. 9).

The triploid catfish produced by the method of this invention are as viable as their diploid full sibs and tolerate the polyploid condition well. We have experienced no difficulty in rearing the triploid fish to 1.5 years.

Figure 7:
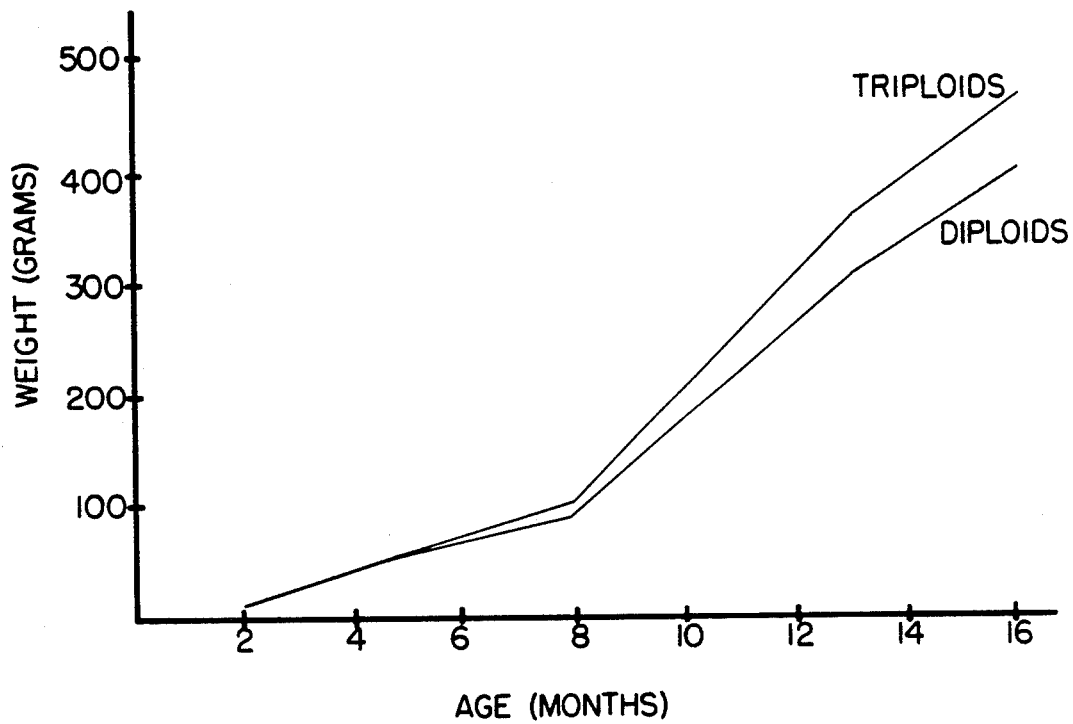
FIG. 7 is a graph showing comparative growth rates of a control group of diploid channel catfish and triploid channel catfish produced according to this invention.

The goal of triploid induction in channel catfish is to increase growth rate and improve feed efficiency. An increase in the growth rates of triploid catfish compared to diploid catfish is shown by our experimental results as shown in the following Table 2 and also in FIG. 7.

TABLE 2

Growth Rates of Diploid and Triploid Channel Catfish, Ictalurus punctatus.

| Age (Months) | WEIGHT [grams ± standard error (SE)] | |
|---|---|---|
|  | Diploid | Triploid |
| 2 | 4.41 | 4.42 |
| 4 | 40.6 ± .2.39 | 40.7 ± 2.11 |
| 8 | 87.8 ± .20 | 92.9 ± .18 |
| 13 | 304.9 ± 17.5 | 357.8 ± 25.9 |
| 16 | 401.67 ± 39.9 | 466.0 ± 63.0 |

Figure 2:
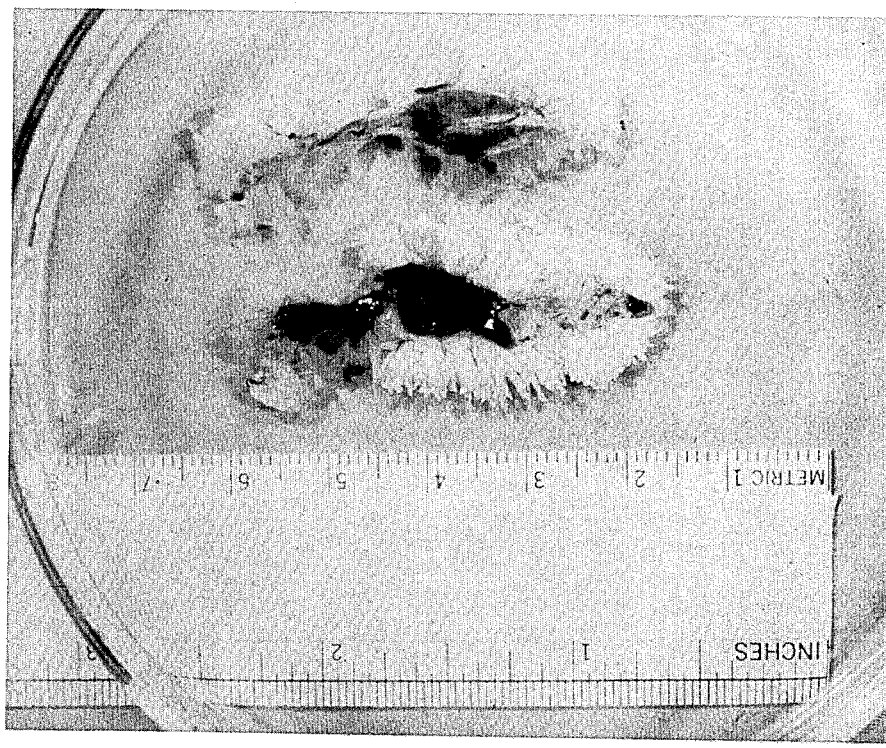
FIG. 2 is a macrophotograph of diploid and triploid testis. Diploid specimen on bottom.

Triploid channel catfish have been found to be sterile. Evidence for sterility is found in macrophotographs (FIGS. 1 and 2) of diploid and triploid ovaries and testes. In each case, the triploid gonads were much smaller, showing no evidence of activity. Microscopic evidence is presented in FIGS. 3 through 6 as histological preparations. The triploid ovarian tissue (FIG. 3) shows little oogenic activity whereas the diploid ovarian tissue (FIG. 4) shows normal follicular development of many oocytes.

FIG. 5 presents the histological section of a testis from a triploid male compared to the tissue section from a diploid male in FIG. 6. Evidence for normal spermatogenesis is lacking in the triploid seminiferous tubules with absence of late meiotic figures and spermatozoa. In addition the seminiferous tubules are irregularly shaped and poorly organized. The diploid testis (FIG. 6) presents seminiferous tubules filled with spermatids/spermatozoa, evidence for completion of normal spermatogenesis.

We claim:

1. The method of induction of triploidy in a channel catfish comprising the steps of:
   securing an egg from a female channel catfish and fertilizing said egg with sperm;
   treating said fertilized egg beginning up to about 5 minutes after fertilization by immersion in water at a temperature of up to about 5° C. for a time up to about 1 hour;
   incubating said egg after said treatment under normal incubation conditions;
   whereby a viable fry is produced that is a triploid channel catfish.

2. A method for production of sterile channel catfish comprising the steps of:
   stripping eggs from a gravid female channel catfish;
   fertilizing said eggs with sperm from mascerated testes of a male channel catfish;
   cold-shocking said fertilized eggs by immersion in water at about 5° C. beginning about 5 minutes after said fertilization step takes place and continuing for no more than 1 hour;
   removing said eggs from said 5° C. water; and
   incubating said eggs after said cold-shocking under normal incubation conditions.

3. The method according to claim 2 in which said eggs are incubated at about 27° C. in aerated flowing water until the catfish fry are hatched.

* * * * *